United States Patent [19]
Wolf et al.

[11] Patent Number: 6,063,914
[45] Date of Patent: May 16, 2000

[54] METHOD OF PRODUCING SWELLABLE, NON-AGING STARCH MALEATES, BIOLOGICALLY DEGRADABLE STARCH MALEATES AS WELL AS USE

[75] Inventors: Heiko Wolf, Oppenheim; Klaus Dorn, Hanau; Thomas Eurich, Frankfurt, all of Germany

[73] Assignee: Stockhausen GmbH & Co. KG, Krefeld, Germany

[21] Appl. No.: 09/013,649

[22] Filed: Jan. 26, 1998

[30] Foreign Application Priority Data

Jan. 25, 1997 [DE] Germany ............................ 197 02 641

[51] Int. Cl.⁷ ..................................................... C08B 31/04
[52] U.S. Cl. .......................... 536/107; 536/110; 536/123; 536/45; 536/48; 536/49
[58] Field of Search ................................. 536/45, 48, 49, 536/151, 110, 123; 604/378, 384, 385.1

[56] References Cited

U.S. PATENT DOCUMENTS 5,789,570  8/1998  Buccholz et al. ....................... 536/107

FOREIGN PATENT DOCUMENTS 688291  3/1953  United Kingdom .

*Primary Examiner*—James O. Wilson
*Assistant Examiner*—Howard Owens
*Attorney, Agent, or Firm*—Pillsbury Madison & Sutro LLP

[57] ABSTRACT

The aging of swellable starch maleates is reduced by reacting with one or more singly and/or multiply functional nucleophiles as in a Michael condensation reaction. Mixtures of mercaptoethanol and 1,2-bis-(2-mercaptoethoxy)-ethane or mixtures of sodium bisulfite and pentaerythrite-tetrakis-(2-mercaptoacetate) are preferred. The decrease of the retention capacity [SRV] in the reaction products after 100 days is preferably <10%. The products find use as biodegradable, non-aging superabsorbers.

24 Claims, No Drawings

METHOD OF PRODUCING SWELLABLE, NON-AGING STARCH MALEATES, BIOLOGICALLY DEGRADABLE STARCH MALEATES AS WELL AS USE

CROSS REFERENCE TO RELATED APPLICATION

This application claims priority from German Application No. 19702641.9, filed Jan. 25, 1997, the subject matter of which is incorporated herein by reference.

FIELD OF THE INVENTION

The invention relates to an absorption material which is based primarily on renewable raw materials, has an improved biological degradability in comparison to the polyacrylates primarily used currently as absorber material and which has improved aging resistance compared with starch maleates suggested for the same purpose.

In particular, the invention relates to a method of producing swellable, non-aging starch materials which have a relatively high absorption capacity and which exhibit only a very slight tendency to gel blocking in comparison to other absorber materials with a polysaccharide base. "Non-aging" refers in this connection to the swelling properties and in particular not to the biological degradability. In addition, the invention discloses absorption material obtainable in accordance with the method of the invention as well as disclosing the use of the products.

BACKGROUND AND PRIOR ART

By far the most of the absorption materials currently in use, frequently also designated as superabsorbers, consist of slightly cross-linked polyacrylates and therefore only a small part, if any, is degradable (see e.g. Stegman et al., Waste Manage. Res. 11 (1993) 155).

In addition to the pure polyacrylates there are also polyacrylates grafted onto stairch (DE-A 26 12 846). However, the starch content of these products (up to 25%) is low. In the case of higher starch contents a distinct deterioration of the absorption properties is observed. Due to the polyacrylate content the biological degradability of these products is also low.

Likewise, up to approximately 25% of a polysaccharide which is water-soluble at least to a limited extent can be worked into a cross-linked polyacrylate superabsorber by introducing the polysaccharide into the reaction mixture during the polymerization of the acrylate (DE-A 40 29 591, DE-A 40 29 592, DE-A-20 29 593).

U.S. Pat. No. 5,079,354 describes an absorber material based on carboxymethyl starch, that is, a starch ether, which is produced by reacting starch with chloroacetic acid. In this process an equivalent amount of sodium chloride relative to the chloroacetic acid used is released, which is undesirable for ecological reasons. In addition, it is known, that etherified polysaccharides are only poorly biodegradable at high degrees of substitution (Mehltretter et al., J. Am. Oil Chem. Soc. 47 (1970) 522).

DE-A 0,603,837 describes the production of starch esters using organic acid anhydrides. To this end starch of diverse origins is allowed to react in a one-stage aqueous process with organic acid anhydrides of general formula I

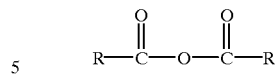

in which R signifies alkyl, aryl, alkenyl, alkaryl or aralkyl with 1 to 7 C atoms under certain conditions of pH, temperature and concentration. Starch esters enumerated by way of example in the specification of EP-A 0,603,837 include starch acetate, starch propionate, starch butyrate, starch hexanoate, starch benzoate or also mixed starch acetates/propionates. In the examples of EP-A 0,603,837 the use of propionic acid anhydride, acetic anhydride and/or butyric acid anhydride is disclosed. The problems which otherwise resulted when using rather large amounts of anhydride such as e.g. the swelling or gelatinization of the starch and problems during separation of the starch esters from the reaction mixture are successfully avoided with the process described in EP-A 0,603,837. The product becomes hydrophobic as a result of the reaction and can therefore be filtered off in a simple manner.

WO 93/01217 (PCT/EP 92/01553) teaches a method of producing starch esters for clinical, especially parenteral application. The starch esters according to WO 93/01217 are quite water-soluble, which is necessary for parenteral application.

There have also already been attempts to create biodegradable superabsorbers. Thus, DE-A 42 06 857 teaches an absorption means consisting of a component based on special, renewable polysaccharide raw materials, of a special, water-swellable polymer, of a matrix material, of an ionic or covalent cross-linking agent and of a reactive addition. The component based on renewable polysaccharide raw materials comprises e.g. guar, carboxymethyl guar, xanthan gum, alginates, gum arabic, hydroxyethyl cellulose or hydroxypropyl cellulose, carboxymethyl cellulose and other cellulose derivatives, starch and starch derivatives such as carboxymethyl starch. It is furthermore known from DE-A 42 06 857 that the cited polymers can be modified by cross-linking in order to reduce their water solubility and to achieve better swelling properties. The cross-linking can take place in the entire polymer or only on the surface of the individual polymer particles.

The conversion of the polymers can take place with ionic cross-linking agents such as e.g. calcium compounds, aluminum compounds, zirconium and iron(III) compounds. Likewise, a conversion is possible with polyfunctional carboxylic acids such as citric acid, mucic acid, tartaric acid, malic acid, malonic acid, succinic acid, glutaric acid, adipic acid, with alcohols such as polyethylene glycols, glycerol, pentaerythrit, propane diols, sucrose, with carbonic acid esters such as glycoldiglycidyl ether, glycol di- or triglycidyl ether and epichlorohydrin, with acid anhydrides such as succinic acid anhydride and maleic acid anhydride, with aldehydes and multifunctional olefins such as bis-(acrylamido) acetic acid and methylene bisacrylamide. Of course, derivatives of the families cited can also be considered as well as heterofunctional compounds with different functional groups of the families cited above.

Although the systems based on sodium carboxymethyl cellulose presented and documented with examples have quite favorable absorption properties in combination with sodium polyacrylate in various tests, no particulars about the biodegradability can be gathered from the publication.

However, it is known that polyacrylates are substantially not biodegradable (R. Stegmann et al., Waste Water Res.

11(2) (1993) p. 155) and carboxymethyl cellulose, a polysaccharide ether, is only very poorly biodegradable (4.6% after 5 days; M. Seekamp, Textilveredlung, Vol. 25 (1990) p. 125.

An absorption material with a biodegradability which is considerably improved in comparison to the polyacrylates primarily used at the time is disclosed in EP-A 0,714,914, which discloses a swellable starch ester which consists of more than 50% by weight of non-water-soluble components and which has a retention capacity for 0.9% by weight aqueous NaCl solution of >500% relative in each instance to the weight of the dry starch ester. The retention capacity is determined in that 0.1 g of the starch ester welded into a nylon bag with a mesh width of 52 μm is allowed to swell for 30 min in 0.9% NaCl solution, the bag is subsequently centrifuged 5 min at 1400 rpm and then any resulting weight increase is gravimetrically determined.

Although the absorption materials presented in EP-A 0,714,914 and based essentially on maleic acid anhydride have very good swelling properties and good biodegradability the starch maleates of EP-A 0,714,914 unfortunately still have distinct disadvantages.

A distinct decrease of the swelling properties occurs after a few weeks. After several weeks very poor swelling properties are obtained both in the measurement of the retention capacity (SRV) and in the determination of the absorption capacity with and without load (AFK5 and A20FK5). This aging has sharply hindered the commercial use of starch maleates as absorption materials in the past.

SUMMARY OF THE INVENTION

In view of the state of the art presented and discussed herein, one object of the invention is to indicate a method of producing swellable and non-aging starch maleales which can be readily carried out. A further object is to produce biodegradable starch maleates which can be obtained in accordance with the process that have an aging with respect to the swelling properties which is reduced. Another object of the invention is the use of swellable, biologically degradable starch maleates which are non-aging with respect to swelling capacity.

It was found within the framework of the invention in a manner which could not have been readily foreseen that swellable starch maleates which are essentially non-aging as regards the swelling properties can be produced by reacting a swellable starch maleate with one or several mono- and/or multifunctional nucleophile(s) as in a Michael condensation reaction.

In particular, material which can be obtained in this manner and is resistant to aging of the swelling properties is suitable for use as an absorption material for the absorption of water, aqueous solutions, dispersions and body fluids for hygiene and animal hygiene uses, especially in diapers and incontinence products as well as in packaging materials for meat and fish, as well as for the improvement of soil, for use in culture containers and as cable jacketings, and in which instances it is also biodegradable.

The starch maleates to be reacted in accordance with the method of the invention are starch esters with a degree of substitution between 0.2 and 2.0, where the degree of substitution indicates the number of substituents per glucose ring. In the case of the esters, pure maleates or mixed esters can be used, that is, in addition to ester groups derived from the maleic acid other ester groups are also present, in an amount up to 98%, preferably, however, only up to 50% and have preferably less than 50%, e.g. 25–49%. Nevertheless, even in the case of the latter compounds and even in the first instance, in which up to 98% other ester groups are present, the term starch maleates is used within the framework of the invention. Basically, however, pure maleates are likewise very well suited for the invention.

The starch maleates are preferably obtained by reacting starch with maleic acid anhydride and, if necessary, with other acid anhydrides. The other anhydrides can be cyclic and/or open-chain anhydrides. However, according to the invention the sole reaction with maleic acid anhydride is by far preferred.

The carboxylic acid anhydrides which are used in an especially advantageous manner together with maleic acid anhydride include, among others, acetic anhydride, propionic acid anhydride and/or succinic acid anhydride.

Although the improvement in the aging resistance can be achieved in accordance with the invention in the case of every swellable starch maleate, swellable starch maleates are reacted in a first preferred method variant according to a method in which starch or modified starch is reacted in a one-stage aqueous reaction with maleic acid anhydride or a mixture of maleic acid anhydride comprising carboxylic acid anhydrides at a pH of 7 to 11 and a temperature of 0 to 40° C.; the pH is maintained in the desired range by the addition of aqueous alkali solution with a concentration of approximately 10 to 50% by weight.

The pH is preferably maintained constant during the reaction of the anhydride or the anhydrides with the starch. The pH should be between 7 and 11 during the reaction. A pH between 8 and 9 is preferred. The pH can be maintained constant in principle by the addition of any desired alkaline material. Alkali hydroxide and alkaline-earth hydroxides as well as the oxides and carbonates of alkali metals and/or of alkaline-earth metals are especially useful. The following are cited by way of example: Sodium hydroxide, potassium hydroxide, calcium hydroxide, ammonium hydroxide, magnesium hydroxide and sodium carbonate. In the production of products with a rather high degree of substitution an alkali solution with a rather high concentration, approximately 10 to 50%, is used in order to avoid an unnecessary dilution of the reaction medium.

An advantageous second modification of the method of the invention provides that a swellable starch maleate is used which can be obtained according to a method in which starch or modified starch is reacted with maleic acid anhydride or with a mixture of maleic acid anhydride comprising carboxylic acid anhydrides in the presence of a base and optionally, also, a solvent, which modification is characterized in that the mixture is allowed to react at a temperature of 80° to 180° C. for 10 min to 10 h and that solvent is tolerated only up to a content of less than 100 parts relative to 100 parts starch.

The use of sodium carbonate as the base is preferred for this embodiment of the method.

In principle, any native, modified or substituted starch can be used as the starch basis of the starch maleate in accordance with the invention. Such starches have been isolated from any vegetable source and comprise e.g. potato starch, corn starch, wheat starch, waxy corn starch and starches with a high amylose content. Starch meal can also be used. Modified products based on one of the starches mentioned above such as e.g. acid-hydrolyzed starch, enzyme-hydrolyzed starch, dextrins and oxidized starch can also be used. Moreover, derivatized starches such as cationic starch, anionic starch, amphoteric starch or non-ionically modified starch such as, e.g., hydroxyethyl starch, can be used. The starches used can be granular or pre-gelatinized starch and the destruction of the granular structure can take place thermally, mechanically or chemically.

The use of starch maleates based on starch soluble in cold water is especially advantageous for the invention. These are, in particular, pre-gelatinized or partially degraded starch, and include, among others, Aeromyl 115™ of the S üdstärke Company.

According to the invention a swellable starch maleate is brought to reaction with one or several nucleophile(s) as in a Michael condensation reaction. An addition of the nucleophile to the double bond of the maleic acid in the starch maleate presumably occurs thereby.

The nucleophiles which can be used for this in accordance with the invention include especially those of general formula I

H—X—R       (I), in which

X represents S or NH, and

R represents hydrogen, a saturated or unsaturated alkyl group with 1 to 18 carbon atoms, which alkyl group is branched or unbranched and can optionally comprise one or several oxygen atoms within the chain and can furthermore be optionally substituted by other functional groups such as e.g. carboxyl, hydroxyl, carbonyl, ester, amide, ether, sulfide, halogen, sulfonic acid, or an aryl group with 6–12 C atoms, which aryl group can be substituted up to four times with carboxyl, hydroxyl, carbonyl, ester, amide, sulfonic acid and/or halogen.

Salts of the compounds of formula I can also be used with particular advantage, in which at least one hydrogen can be replaced by an alkali metal or an alkaline earth metal. A corresponding compound is, e.g., $Na_2S$.

Sulfurous acid and its salts also are among the compounds which can be used in accordance with the invention. Sodium bisulfite and sodium hydrogen sulfite are especially preferred.

Nucleophiles of general formula II

H—X—R—Y—H       (II)

can also be used in accordance with the invention in an especially favorable manner, in which X and R have the significance indicated for formula I and Y represents independently of X, S or NH. Salts can also be used from compounds of formula II as in the case of formula I compounds.

In so far as optically active forms exist for the compounds of formulas I or II which can be used in accordance with the invention, they belong both individually as well as in a mixture, e.g. as enantiomers, diastereomers or racemates, to the invention.

The nucleophiles of general formula I as well as of general formula II are added in the sense of a Michael-analogous addition to the double bond of the maleic acid structural elements present in the starch maleates. Amines and especially thiols are preferred in this connection. Especially in the case of the thiols, no additional catalysts are generally necessary in order to make possible a rapid addition to the double bonds.

Based on these conditions, the method of the invention is characterized in another especially preferred embodiment in that a compound containing SH groups, such as a thiol, is used as nucleophile.

It is noteworthy that the effect of hindering the aging of starch maleates in accordance with the invention takes place both in the case of the monofunctional structural elements of general formula I by blocking the double bond of the maleate group as well as in the case of the difunctional structural elements of general formula II by cross-linking, and therewith also blocking the double bond of the maleate group.

The individual monofunctional structural elements which can be used within the framework of the method of the invention include, among others, amino acids (both α- and others) such as glycine, alanine, valine, leucine, isoleucine, serine, threonine, asparaginic acid, asparagine, glutamic acid, glutamine, proline, histidine, tryptophane, phenylalanine, tyrosine, methionine; linear and branched amines such as ethylamine, propylamine, butylamine, sec.-butylamine, tert.-butylamine, isobutylamine, pentylamine, isopentylamine, 2-aminopentane, hexylamine, heptylamine, 2-heptylamine, octylamine, tert.-octylamine, nonylamine, decylamine, undecylamine, dodecylamine, ethanolamine, 3-amino-1-propanol, 1-amino-2-propanol, alaninol, 2-amino-1-butanol, 4-amino-1-butanol, 2-amino-2-methyl-1-propanol, 5-amino-1-pentanol, valinol, leucinol, tert.-leucinol, N-propylethylene diamine, 2-ethylamino-ethylamine; linear and branched thiols such as ethanethiol, 1-propanethiol, 2-propanethiol, 1-butanethiol, sec.-butyl mercaptan, tert.-butyl mercaptan, isobutyl mercaptan, 1-pentanethiol, 1-hexanethiol, 1-heptanethiol, 1-octanethiol, 1-nonanethiol, 1-decanethiol, 1-undecanethiol, 1-dodecanethiol, tert.-dodecanethiol, 1-tetradecanethiol, 1-hexadecanethiol, 1-octadecanethiol, mercapto ethanol, 3-mercapto-1-propanol, 4-mercapto-1-butanol, 3-mercapto-2-butanol, 6-mercapto-1-hexanol, 8-mercapto-1-octanol, 10-mercapto-1-decanol, 11-mercapto-1-undecanol, mercaptoacetic acid and its salts and esters, 3-mercaptopropionic acid and its salts and esters, 11-mercaptoundecanoic acid and its salts and esters, mercaptoethane sulfonic acid and its salts, 3-mercapto-1-propane sulfonic acid and its salts, mercaptopyruvic acid and its salts, 2-diethylamino ethanethiol (-hydrochloride), 3-mercaptopropylmethyldimethoxysilane, 3-mercaptopropyltriethoxysilane, 3-mercaptopropyltrimethoxysilane, N-methylmercaptoacetamide, mercaptophenol.

The use of mercaptoethanol, 3-mercapto-1-propanol, mercaptoacetic acid, 3-mercaptopropionic acid, mercaptoethane sulfonic acid and mercaptopropane sulfonic is especially preferred.

The difunctional cross-linking molecules which can be used within the framework of the invention include, among others, amino acids with additional amino- or thiol groups such as cysteine, penicillamine, lysine, ornithine, arginine, linear or branched diamines such as diaminoethane, 1,2-diamino-propane, 1,3-diaminopropane, 1,4-diaminobutane, 1,2-diamino-2-methylpropane, 1,5-diaminopentane, 1,3-diaminopentane, 1,3-diamino-2,2-dimethylpropane, 1,6-diaminohexane, 1,5-diamino-2-methylpentane, 1,7-diaminoheptane, 1,8-diaminooctane, 1,9-diaminononane, 1,10-diaminohexane, 1,12-diaminododecane, 1,2-bis-(2-aminoethoxy)ethane, bis-(2-aminoethyl)ether;

dithiols such as ethanedithiol, 1,3-propanedithiol, 1,4-butanedithiol, 2,3-butanedithiol, 1,5-pentanedithiol, 1,6-hexanedithiol, 1,7-heptanedithiol, 1,8-octanedithiol, 1,9-nonanedithiol, 1,10-decanedithiol, 1,11-undecanedithiol, 1,12-docecanedithiol, 1,16-hexadecanedithiol;

aminothiols such as cysteamine, 2-mercapto-isobutylamine; bis-(2-mercaptoethyl)ether, bis-(2-mercaptoethyl)sulfide, 1,2-bis-(2-mercaptoethoxy)-ethane (MEE), N-(2-mercaptopropionyl)-glycine, 2,3-dimercapto-succinic acid, 2,3-dihydroxy-1,4-butanedithiol, 2,3-dimercapto-1- propanol, 2,3-dimercapto-propane sulfonic acid and its salts, lipoic acid (reduced form), pentaerythritol-tetrakis-(3-mercapto-propionate), pentaerythritol-tetrakis-(2-mercaptoacetate), mixed esters of 2-mercaptoacetic acid and of 3-mercaptoacetic acid with pentaerythritol, hydrogen sulfide, sodium sulfide, 1,3-dimercaptobenzene, o-benzol, thioresorcinol, 1,2-dimercaptobenzene, toluene-3,4-dithiol, oligosulfides with terminal thiol groups such as polymethylene tetrasulfide (Thiokol products of the Morton company), and oligo- and polypeptides with at least two free amino groups and/or thiol groups.

The following are especially preferred for the use as the nucleophile within the framework of the method of the invention: 1,2-bis-(2-mercaptoethoxy)ethane) (MEE), 2,3-dimercaptosuccinic acid, cysteine, cysteamine, 2,3-dihydroxy-1,4-butane dithiol, pentaerythritol-tetrakis-(3-mercaptopropionate), pentaerythritol-tetrakis-(2-mercaptoacetate), bis-(2-mercaptoethyl)-ether, bis-(2-mercaptoethyl)-sulfide.

An especially favorable effect can be achieved within the framework of the invention by combining a difunctional cross-linking agent (nucleophile of formula II) and a monofunctional structural element (nucleophile of formula I). The best swelling properties with the most extensive prevention of the aging of starch maleates are realized with the combined use of a monofunctional with a difunctional structural element. Thus, the method of the invention is characterized in a further, quite especially advantageous variation using a mixture of mercaptoethanol (ME) and 1,2bis-(2-mercaptoethoxy)ethane (MEE) or a mixture of pentaerythrite-tetrakis-(2-mercaptoacetate) and sodium bisulfite. In particular, network make-up and aging stability can be combined with one another in a simple manner by the cross-linking of starch maleates with di- or oligothiols and the reaction of any residual maleate double bonds with thiols or sodium bisulfite.

It is therefore also advantageous for the method of the invention to use between 0.001 and 0.5 equivalents of mercaptoethoxyethane (MEE) in combination with between 0.5 and 0.999 equivalents of mercaptoethanol (ME) as nucleophile, which equivalents refer to the amounts of maleic acid anhydride contained in the starch maleate. In this manner good swelling values can be adjusted as regards the SRV and the free swelling within this concentration of cross-linking agent and blocking agent. Excellent ranges are located between 0.001 and 0.03 eq MEE and 0.97 and 0.999 ME.

It is furthermore advantageous for the method to use between 0.001 and 0.5 equivalents of pentaerythrite-tetrakis-(2-mercaptoacetate) (PTMA) in combination with between 0.25 and 0.999 equivalents of sodium bisulfite as nucleophile, which equivalents refer to the amounts of maleic acid anhydride contained in the starch maleate. In this manner good swelling values can be adjusted as regards the SRV and the free swelling within this concentration of cross-linking agent and blocking agent. Excellent ranges are located between 0.001 and 0.03 equivalents of PTMA and 0.4 and 0.9 equivalents of sodium bisulfite.

Although the reaction of starch maleates with nucleophiles can be carried out within the framework of the invention with starch maleates of any origin, the method of the invention nevertheless demonstrates its special advantages in particular if the starch maleates are treated in a swollen or dissolved state with a nucleophile. For this reason the reaction can be carried out without isolation of intermediates, in particular following the actual synthesis reaction of the starch maleates. To this extent it is a preferred variation of the methlod of the invention if the reaction is carried out with the one and/or several singly and/or multiply functional nucleophile(s) immediately following the synthesis of the starch maleate in a one-pot reaction at temperatures between room temperature and approximately 80° C. over a time period of 10 min to 24 h, preferably between 10 min and 10 h.

Network make-up and aging stability can be optimally combined with one another and monitored in particular by this extremely simple procedure within the framework of the invention by means of the cross-linking of the starch maleates preferably with dithiols and by the reaction of the residual maleate double bonds preferably with thiols.

Degradable starch maleates obtainable in accordance with the method described herein are also subject matter of the invention. They are characterized by the exceedingly favorable aging behavior simultaneously with good swelling properties. In particular the biodegradable starch maleates of the invention are characterized in that a decrease of the SRV can be determined after 100 days of less than 20%. Furthermore, especially preferred starch maleates in accordance with the invention are those exhibiting a decrease of the SRV after 100 days of less than 10%.

An especially advantageous procedure provides a reduction of the gel blocking of the superabsorber particles produced. As is generally known about superabsorber particles, slightly cross-linked products display a greater absorption of liquid than do strongly cross-linked ones; however, they also tend to a greater extent toward gel blocking, especially upon absorption under load. In order to prevent the gel blocking of slightly cross-linked gels, a starch maleate is reacted in accordance with the invention with a compound of formula I and/or formula II or with a mixture in such a manner that a slightly cross-linked gel is produced whose maleate double bonds are reacted only in part. After the drying and comminution the product is suspended in a solvent or solvent mixture in which a cross-linking agent of formula II or a mixture of compounds according to formula II and formula I is dissolved. According to this method an additional cross-linking takes place primarily on the surface of the particles. After this treatment the superabsorber gels display a distinctly lesser tendency toward gel blocking yet retain a significantly better absorption capacity than gels which are highly cross-linked throughout.

Organic solvents miscible with water are suitable as solvents for the subsequent cross-linking in accordance with the invention. Alcohols such as methanol, ethanol, and i-propanol and their mixtures with water in a ratio of 50:50 to 99:1 are preferred. Mixtures of ethanol with water in a ratio of 70:30 to 99:1 are especially preferable.

The invention also includes a process for using the specified starch maleates in an amount of 100 parts by weight together with 0.7 to 70 parts by weight of an antiblocking agent based on natural or synthetic, preferably hydrophilic fibers or materials with a large surface as suberabsorbers. The use of starch maleate as superabsorber together with 1 to 5 parts by weight silicic acid or cellulose fibers as antiblocking agent is preferred. The starch ester of the invention finds further use as an absorption agent for the absorption of water, aqueous solutions, dispersions and body fluids in hygiene and animal hygiene, especially in diapers, tampons and incontinence products as well as in packaging materials for meat and fish, as absorption material for the absorption of water and aqueous solutions in culture containers and for soil improvement or as absorption material for the absorption of water and aqueous solutions in cable jacketings.

In order to further improve the behavior under pressure loading in non-aging starch maleates in accordance with the invention it is furthermore especially advantageous to subsequently cross-link the particle surface of the starch maleates. This can prevent a gel blocking with retention of good values in the SRV and AFK5.

DETAILED DESCRIPTION OF THE INVENTION

The invention is explained in detail in the following with reference made to exemplary embodiments.

I) Methods

A) Determination of the Substitution Yield via the Consumption of NaOH During Synthesis In the reaction of starch with maleic acid anhydride (MSA) in aqueous solution one mole NaOH is used per mole maleic acid anhydride. If no addition of the maleic acid anhydride to the starch takes place but rather a hydrolysis to disodium maleate then 2 moles NaOH are used per mole MSA with the pH being maintained constant. If no non-reacted anhydride is present any more at the end of the reaction the degree of substitution can be calculated according to $$DS(NaOH) = Ds_{theoret}\left(1 - \frac{\text{consumption of NaOH in moles} - \text{amount MSA used in moles}}{\text{amount MSA used in moles}}\right)$$

in which $$DS_{theoret} = \frac{\text{amount MSA in moles used}}{\text{amount starch used in moles}_{monosaccharide}}.$$

B) Method of Determining the Saline Retention Capacity (SRV)

A tea bag test was carried out to determine the retention capacity. To this end 0.10 g of the test substance is weighed into a bag of nylon fabric with a mesh width of 52 $\mu$m. The welded nylon bag is placed into a 0.9% solution of NaCl and the test material allowed to swell for 30 minutes. The bag is subsequently removed and centrifuged 5 minutes at 1400 rpm in a centrifuge tray with sieve plate. The absorption of liquid is determined gravimetrically and converted to 1 g of the substance to be tested. The value obtained in this manner is designated as the retention capacity (abbreviated as SRV for "saline retention value").

C) Method for Determining the Absorption Capacity with and without Load (AFK5, A20FK5)

5 parts precipitated silicic acid (FK500 LS, Degussa) are mixed with 95 parts of the substance to be examined. This mixture is designated below as the "test substance".

0.5 g test substance are placed onto a G3 sintered-glass-fit filter 3 cm in diameter. The filter is connected via a hose to a burette filled with 0.9% solution of NaCl. The amount of liquid which the test substance soaks up in 10 min is determined. During the duration of the test the burette is refilled in such a manner that the meniscus is always at the height of the glass-fit filter. The value determined in this manner is converted to 1 g test substance and designated with AFK5.

In order to determine the absorption capacity under load (A20FK5) a weight, exerting a pressure of 20 g/cm$^2$ is additionally placed on the test substance in the embodiment described above. The value obtained in this manner is likewise converted to 1 g test substance.

II) EXAMPLES AND REFERENCE EXAMPLES

Example 1

Synthesis of Starch Maleate 50 g (=0.278 mol) Aeromyl 115 (physically modified starch, soluble in cold water, of the Südstärke company; residual moisture=approximately 9.5%) are dissolved in 400 ml water. The pH is adjusted with 3 N NaOH to a pH of 8 and maintained constant during the reaction. 27.2 g (=0.278 mol) solid maleic acid anhydride is added over a period of 2 h at a reaction temperature of 0° C. The mixture is agitated for a further hour during which the reaction mixture is brought to room temperature (postreaction). The degree of substitution (DS(NaOH)) is 0.88.

Example 2

Synthesis of Starch Maleate 50 g (=0.278 mol) Aeromyl 115 (physically modified starch, soluble in cold water, of the Südstärke company; residual moisture=approximately 9.5%) are dissolved in 400 ml water. The pH is adjusted with 3 N NaOH to a pH of 8 and maintained constant during the reaction. 40.91 g (=0.417 mol) solid maleic acid anhydride is added over a period of 2 h at a reaction temperature of 0° C. The mixture is agitated for a further hour during which the reaction mixture is brought to room temperature (postreaction). The degree of substitution (DS(NaOH)) is 1.15.

Examples 3–8

Immediately after the one-hour postreaction of the starch maleate of example 1 the mixture is heated to 60° C. and a mixture of cross-linking agent consisting of 1,2-bis-(2-mercaptoethoxy-ethane) (MEE) and/or mercaptoethanol (ME) is added to the reaction mixture in the amounts indicated in Table 1. The pH during the addition is between 7 and 8. The mixture is homogenized and the agitator mechanism cut off. After approximately 1 minute gel formation occurs. The mixture is allowed to postreact 3 h at 60° C. and the reaction mixture is cooled down overnight. The water is evaporated using Rotavapor at 80° C. in a vacuum and the product is dried overnight in a vacuum drying oven until constancy of weight is obtained. The starch maleate obtained in this manner is comminuted and ground. The absorption capacity (AFK5; A20FK5) and the retention capacity (SRV) of the product obtained in this manner are determined. The measurements are repeated after storage (see Table 1). Table 1 shows the changes in the SRV since experience has shown that the aging effects occur most distinctly there (see the reference examples too).

The cross-linking with MEE/ME can also be carried out at room temperature. The time until gel formation is then extended to 20–45 minutes. Postreaction at room temperature overnight and workup are carried out in the same manner.

TABLE 1

Survey of the synthesized products. The indications of amount in the column headed "Explanation" correspond to molar equivalents (eg) relative to maleic acid anhydride. The drying took place at 80° C.

| Ex. | Explanation | SRV (g/g) initial value | SRV (g/g) after (x) days | Deviation (%) |
|---|---|---|---|---|
| 3 | starch maleate, 0.5 eq MEE | 5.6 | 5.6 (128) | 0 |
| 4 | starch maleate, 0.25 eq MEE 0.5 eq ME | 5.3 | 5.4 (128) | +2 |

TABLE 1-continued

Survey of the synthesized products. The indications of amount in the column headed "Explanation" correspond to molar equivalents (eg) relative to maleic acid anhydride. The drying took place at 80° C.

| Ex. | Explanation | SRV (g/g) initial value | SRV (g/g) after (x) days | Deviation (%) |
|---|---|---|---|---|
| 5 | starch maleate, 0.1 eq MEE 0.8 eq ME | 7.9 | 9.5 (122) | −5 |
| 6 | starch maleate, 0.03 eq MEE | 15.9 | 14.1 (127) | −11 |
| 7 | starch maleate, 0.01 eq MEE 0.99 eq ME | 12.5 | 12.4 (115) | −1 |
| 8 | starch maleate, 0.005 eq MEE 0.98 eq ME | 13.3 | 12.9 (115) | −3 |

Example 9

Synthesis of a Mixed Starch Ester 50 g (=0.278 mol) Aeromyl 115 (physically modified starch, soluble in cold water, of the Südstärke company; residual moisture=approximately 9.5%) are dissolved in 400 ml water. The pH is adjusted with 3 N NaOH to a pH of 8 and maintained constant during the reaction. A mixture of 1.088 g (0.011 mol) solid maleic acid anhydride and of 26.71 g (0.2668 mol) solid succinic acid anhydride is added over a period of 2 h at a reaction temperature of 0° C. The mixture is agitated for a further hour during which time the reaction mixture is brought to room temperature (postreaction). The degree of substitution (DS(NaOH)) is 0.88.

Immediately after the one-hour postreaction time of the starch maleate the mixture is heated to 60° C. and 0.506 g (0.00278 mol) of the cross-linking agent 1,2-bis-(2-mercaptoethoxy-ethane) (MEE) is added to the reaction mixture. The pH during the addition is between 7 and 8. The mixture is homogenized and the agitator mechanism cut off. Gel formation occurs after approximately 25 minutes. The mixture is allowed to postreact 3 h at 60° C. and the reaction mixture is cooled off overnight. The water is evaporated using a Rotavapor at 45° C. in a vacuum and the product is dried overnight in a vacuum drying oven until constancy of weight is obtained. The starch maleate obtained in this manner is comminuted and ground.
SRV=23.4 g/g Example 10

The product of example 9 is mixed with 5% of precipitated silicic acid (FK500LS, Degussa AG).
AFK5=10.2 ml/g; A20FK5=3.4 ml/g Example 11

100 g (=0.568 mol) Aeromyl 115 (physically modified starch, soluble in cold water, of the Südstärke company; residual moisture=approximately 7.9%) are dissolved in 800 ml water. The pH is adjusted with 3 N NaOH to a pH of 8 and maintained constant during the reaction. 55.7 g (=0.568 mol) solid maleic acid anhydride is added over a period of 2 h at a reaction temperature of 0° C. The mixture is agitated for a further hour during which the reaction mixture is brought to room temperature (postreaction). The degree of substitution (DS(NaOH)) is 0.86. 48.6 g sodium bisulfite in 100 ml water and 3.11 g 1,2-bis-(2-mercaptoethoxy-ethane) (MEE) in 25 ml ethanol are subsequently added. The mixture is homogenized and the agitator mechanism cut off. The mixture is allowed to postreact overnight. The water is evaporated using a Rotavapor at 80° C. in a vacuum and the product dried overnight in a vacuum drying oven until constancy of weight is obtained. The starch maleate obtained in this manner is comminuted and ground.
SRV=17.4 g/g; AFK5=20.6 ml/g; A20FK5=3.9 ml/g
SRV after 126 days=16.0 g/g (−8%)

Example 12

100 g (=0.568 mol) Aeromyl 115 (physically modified starch, soluble in cold water, of the Südstärke company; residual moisture=approximately 7.9%) are dissolved in 800 ml water. The pH is adjusted with 3 N NaOH to a pH of 8 and maintained constant during the reaction. 27.8 g (=0.284 mol) solid maleic acid anhydride is added over a period of 2 h at a reaction temperature of 0° C. The mixture is agitated for a further hour during which the reaction mixture is brought to room temperature (postreaction). The degree of substitution (DS(NaOH)) is 0.48. 24.3 g sodium bisulfite in 100 ml water and 3.69 g pentaerythrite-tetrakis-(2-mercaptoacetate) (PTMA) in 25 ml THF are subsequently added. The mixture is homogenized and the agitator mechanism cut off. The mixture is allowed to postreact overnight. The water is evaporated using a Rotavapor at 80° C. in a vacuum and the product dried overnight in a vacuum drying oven until constancy of weight is obtained. The starch maleate obtained in this manner is comminuted and ground.
SRV=14.2 g/g; AFK5=21.3 ml/g; A20FK5=6.4 ml/g
SVR after 106 days=12.6 g/g (−11%)

Example 13

100 g (=0.568 mol) Aeromyl 115 (physically modified starch, soluble in cold water, of the Südstärke company; residual moisture=approximately 7.9%) is dissolved is 800 ml water. The pH is adjusted with 3 N NaOH to a pH of 8 and maintained constant during the reaction. 27.8 g (=0.284 mol) solid maleic acid anhydride are added over a period of 2 h at a reaction temperature of 0° C. The mixture is agitated for a further hour during which the reaction mixture is brought to room temperature (postreaction). The degree of substitution (DS(NaOH)) is 0.45. 24.3 g sodium bisulfite in 100 ml water are subsequently added. The reaction mixture is heated to 40° C. and 1.84 g pentaerythrite-tetrakis-(2-mercaptoacetate) (PTMA) in 25 ml THF are added. The mixture is homogenized and the agitator mechanism cut off. The mixture is allowed to postreact 2 h at 40° C. and overnight at room temperature. The product is dried at 50° C. in a circulating-air drying oven. The starch maleate obtained in this manner is comminuted and ground.
SRV=17.5 g/g; AFK5=19.2 ml/g; A20FK5=3.8 ml/g
SRV after 118 days=15.7 g/g (−10%)

Example 14

100 g (=0.568 mol) Aeromyl 115 (physically modified starch, soluble in cold water, of the Südstärke company; residual moisture=approximately 7.9%) is dissolved in 800 ml water. The pH is adjusted with 3 N NaOH to 8 and maintained constant during the reaction. 27.8 g (=0.284 mol) solid maleic acid anhydride are added over a period of 2 h at a reaction temperature of 0° C. The mixture is agitated for a further hour during which the reaction mixture is brought to room temperature (postreaction). The degree of substitution (DS(NaOH)) is 0.45. 21.3 g sodium bisulfite in 100 ml water are subsequently added. The reaction mixture is heated to 60° C. and 1.84 g pentaerythrite-tetrakis-(2-mercaptoacetate) (PTMA) in 25 ml THF are added. The mixture is homogenized and the agitator mechanism cut off. The mixture is allowed to postreact 2 h at 40° C. and overnight at room temperature. The product is dried at 50° C. in a circulating-air drying oven. The starch maleate obtained in this manner is comminuted and ground.
SRV=15.8 g/g; AFK5=20.8 ml/g; A20FK5=4.1 ml/g
SRV after 112 days=14.6 g/g (−8%)

Example 15

100 g (=0.568 mol) Aeromyl 115 (physically modified starch, soluble in cold water, of the Südstärke company; residual moisture=approximately 7.9%) is dissolved in 800 ml water. The pH is adjusted with 3 N NaOH to a pH of 8 and maintained constant during the reaction. 27.8 g (=0.284 mol) solid maleic acid anhydride are added over a period of 2 h at a reaction temperature of 0° C. The mixture is agitated for a further hour during which the reaction mixture is brought to room temperature (postreaction). The degree of substitution (DS(NaOH)) is 0.45. Subsequently 24.3 g sodium bisulfite in 100 ml water and 0.92 g pentaerythrite-tetrakis-(2-mercaptoacetate) (PTMA) in 25 ml THF is subsequently added. The mixture is homogenized and the agitator mechanism cut off. The mixture is allowed to postreact overnight. The water is drawn off on a Rotavapor at 80° C. in a vacuum and the product dried overnight in a vacuum drying oven until constancy of weight is obtained. The starch maleate obtained in this manner is comminuted and ground.
SRV=20.6 g/g; AFK5=21.2 ml/g; A20FK5=4.2 ml/g
SRV after 706 days=78.0 g/f (−13%)

Reference Example 1

The reaction solution of example 1 is rotated in and subsequently dried in a vacuum drying oven. The product is ground and again dried 30 min at 100° C. in a vacuum drying oven.
SRV=14.3 g/g

Reference Example 2

The product of reference example 1 is mixed with 5% of a precipitated silicic acid (FK500LS, Degussa AG).
AFK5=21.1 ml/g; A20FK5=7.6 ml/g

Reference Example 3

50 g (=0.278 mol) Aeromyl 115 (physically modified starch, soluble in cold water, of the Südstärke company; residual moisture=approximately 9.5%) is dissolved in 400 ml water. The pH is adjusted with 3 N NaOH to a pH of 8 and maintained constant during the reaction. 27.27 g (=0.278 mol) solid maleic acid anhydride are added over a period of 2 h at a reaction temperature of 0° C. The mixture is agitated for a further hour during which the reaction mixture is brought to room temperature. The mixture is subsequently allowed to postreact another 2 h at 60° C. The degree of substitution (DS(NaOH)) is 0.76. The reaction solution is rotated in and subsequently dried in a vacuum drying oven. The product is ground and reground for 30 min at 100° C. in the vacuum drying oven.
SRV=12.6 g/g

Reference Example 4

50 g (=0.278 mol) Aeromyl 115 (physically modified starch, soluble in cold water, of the Südstärke company; residual moisture=approximately 9.5%) is dissolved in 400 ml water. The pH is adjusted with 3 N NaOH to a pH of 8 and maintained constant during the reaction. 13.6 mg benzoquinone are added. 27.27 g (=0.278 mol) solid maleic acid anhydride is added over a period of 2 h at a reaction temperature of 0° C. The mixture is agitated for a further hour during which the reaction mixture is brought to room temperature (postreaction). The degree of substitution (DS (NaOH)) is 0.83. The reaction solution is rotated in and subsequently dried in a vacuum drying oven. The product is ground and reground for 30 min at 100° C. in the vacuum drying oven.
SRV=19.4 g/g Aging of the substances of the reference examples Measurements of the products of the reference examples were repeated after storage (see Table 2).

TABLE 3

| Ref. Example | SRV initial value | SRV after (x) days | Deviation (%) |
| --- | --- | --- | --- |
| 1 | 14.3 | 10.7 (84) | −25 |
| 3 | 12.6 | 9.7 (84) | −23 |
| 4 | 19.4 | 10.0 (84) | −48 |

What is claimed is:

1. A method of producing starch maleates, comprising:
   reacting a swellable starch maleate with at least one multifunctional nucleophile or with a mixture of at least one multifunctional nucleophile and at least one monofunctional nucleophile, to thereby obtain a swellable, starch maleate.
2. The method according to claim 1, wherein the reacting step comprises a Michael condensation reaction.
3. The method according to claim 1, wherein the swellable starch maleate is obtained according to a method comprising:
   reacting starch or modified starch in a one-stage aqueous reaction with maleic acid anhydride or a mixture of maleic acid anhydride comprising carboxylic acid anhydrides at a pH of 7 to 11 and a temperature of 0 to 40° C., and
   maintaining the pH in the desired range by addition of aqueous alkali solution wherein said aqueous alkali solution has a concentration of approximately 10 to 50% by weight.
4. The method according to claim 1, wherein the swellable starch maleate is obtained according to a method comprising:
   reacting starch or modified starch with maleic acid anhydride or with a mixture of maleic acid anhydride comprising carboxylic acid anhydrides in the presence of a base and optionally of a solvent, and
   reacting the mixture at a temperature of 80° to 180° C. for 10 min to 10 h with solvent, if present only up to a content of less than 100 parts relative to 100 parts starch.
5. The method according to claim 4, wherein the base comprises sodium carbonate.
6. The method according to claim 1, wherein the nucleophile comprises a compound containing SH groups.
7. The method according to claim 6, wherein the nucleophile comprises mercaptoethanol.
8. The method according to claim 6, wherein the nucleophile comprises 1,2-bis-(2-mercaptoethoxy)-ethane.
9. The method according to claim 6, wherein the nucleophile comprises a mixture of mercaptoethanol and 1,2-bis-(2-mercaptoethoxy)-ethane.

10. The method according to claim 9, wherein the nucleophile comprises between 0.001 and 0.5 equivalents of mercaptoethanol, wherein equivalents refers to the amounts of maleic acid anhydride contained in the starch maleate.

11. The method according to claim 1, wherein the nucleophile comprises sodium bisulfite or sodium hydrogen sulfite.

12. The method according to claim 1, wherein the nucleophile comprises pentaerythrite-tetrakis-(2-mercaptoacetate).

13. The method according to claim 1, wherein the nucleophile comprises a mixture of sodium bisulfite or sodium hydrogen sulfite and pentaerythrite-tetrakis-(2-mercaptoacetate).

14. The method according to claim 13, wherein the nucleophile comprises between 0.001 and 0.5 equivalents of pentaerythrite-tetrakis-(2-mercaptoacetate) in combination with between 0.25 and 0.999 equivalents of sodium bisulfite, wherein equivalents refers to the amounts of maleic acid anhydride contained in the starch maleate.

15. The method according to claim 1, further comprising synthesizing the starch maleate in a one-pot reaction at temperatures between room temperature and approximately 80° C. over a time period of 10 min to 24 hrs immediately prior to carrying out the reacting step.

16. The method according to claim 1, comprising:
reacting the swellable starch maleate wherein only a part of double bonds react,
isolating the starch maleate;
suspending the starch maleate in a solvent; and
subsequently cross-linking the suspended starch maleate on its surface.

17. Biodegradable starch maleate obtainable according to the method of claim 1, characterized by a decrease of the saline retention value after 100 days of less than 20%, wherein said biodegradable starch maleate comprises a superabsorbent.

18. The starch maleate according to claim 17, wherein the decrease of the saline retention value after 100 days is less than 0%.

19. A superabsorbent comprising the starch maleate according to claim 17, in an amount of 100 parts by weight together with 0.7–70 parts by weight of an antiblocking agent based on natural or synthetic fibers.

20. A superabsorbent comprising starch maleate according to claim 17 together with an antiblocking agent comprising 1–5 parts by weight silicic acid or cellulose fibers.

21. A process for absorbing an aqueous liquid from a product having starch maleate superabsorbent according to claim 17, comprising:
obtaining a product comprising said biodegradable starch maleate superabsorbent and
absorbing an aqueous medium in the superabsorbent,
wherein said product is a member selected from the group consisting of diapers, incontinence products and packaging materials for meat or fish.

22. A process for absorbing aqueous liquids from a culture container, comprising:
obtaining a culture container,
introducing biodegradable starch maleate superabsorbent according to claim 17 to said culture container, and
absorbing into the superabsorbent an aqueous medium present in said culture container.

23. A process for absorbing aqueous liquids from cable jacketings, comprising:
providing cable jacketings comprising biodegradable starch maleate superabsorbent according to claim 17 and
absorbing an aqueous medium present in cable jacketings into the superabsorbent.

24. A process for improving soil, comprising:
providing soil in the presence of biodegradable starch maleate superabsorbent according to claim 17, and
absorbing an aqueous medium in soil into the superabsorbent for soil improvement.

* * * * *